(12) United States Patent
Du Toit

(10) Patent No.: US 6,319,477 B1
(45) Date of Patent: Nov. 20, 2001

(54) OXYGEN GENERATING DEVICE

(75) Inventor: William Du Toit, Stellenbosch (ZA)

(73) Assignee: Advent Aerobe Ltd., Grand Caymans (KY)

( * ) Notice: Subject to any disclaimer, the term of this patent is extended or adjusted under 35 U.S.C. 154(b) by 0 days.

(21) Appl. No.: 09/239,579

(22) Filed: Jan. 29, 1999

(30) Foreign Application Priority Data

Jan. 21, 1999 (ZA) .................................................. 990535

(51) Int. Cl.[7] .............................. A62B 7/08; B01D 47/02; C10J 1/08
(52) U.S. Cl. ........................ 422/120; 261/121.1; 261/124
(58) Field of Search .................................. 422/122, 120, 422/126; 261/121.1, 122.1, 124.1, DIG. 65

(56) References Cited

U.S. PATENT DOCUMENTS

| | | | | |
|---|---|---|---|---|
| 3,615,252 | * | 10/1971 | DiPietro | 23/282 |
| 3,986,838 | * | 10/1976 | Reichert | 23/281 |
| 4,246,229 | * | 1/1981 | McBride et al. | 422/122 |
| 4,310,502 | * | 1/1982 | Wagner | 423/579 |
| 4,318,895 | * | 3/1982 | Richardson et al. | 423/579 |
| 4,342,725 | * | 8/1982 | Collins | 422/126 |
| 4,548,730 | * | 10/1985 | Koslow | 252/186.43 |
| 5,102,627 | * | 4/1992 | Plester | 422/112 |
| 5,540,218 | * | 7/1996 | Jones et al. | 128/201.24 |
| 5,620,664 | * | 4/1997 | Palmer | 422/122 |
| 5,809,210 | * | 9/1998 | Moore et al. | 392/402 |
| 5,985,113 | * | 11/1999 | Crome et al. | 204/286 |

* cited by examiner

Primary Examiner—Robert J. Warden, Sr.
Assistant Examiner—Monzer R. Chorbaji
(74) Attorney, Agent, or Firm—Baker, Donelson, Bearman & Caldwell

(57) ABSTRACT

The present invention is a oxygen generating device which comprises:

a container having a mouth and a neck surrounding the mouth; a tank which has an annual flange for establishing a gas tight seal between the tank and the neck;

a dome assembly which is engageable with the neck and extends upwardly to define a dome chamber above the neck; and means for permitting oxygen generated in the tank to flow into the dome chamber by bubbling through a liquid contained in the dome base;

the dome base having an outlet connection through which oxygen can leave the chamber and where at least part of the dome is transparent so as to render the inside thereof visible from the outside of the dome.

8 Claims, 2 Drawing Sheets

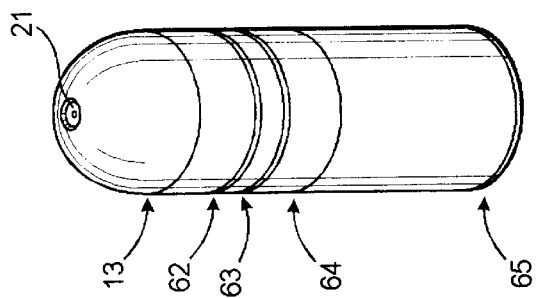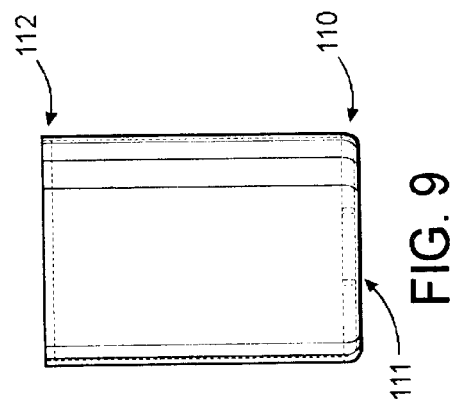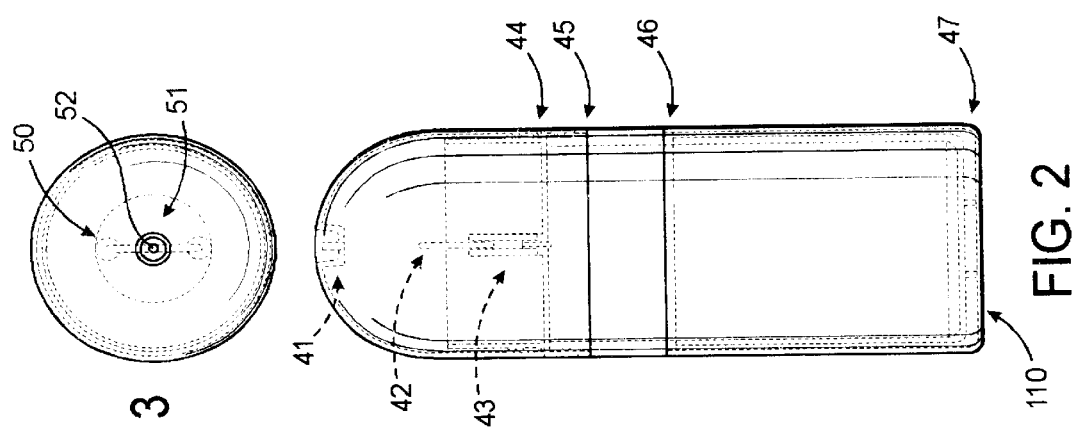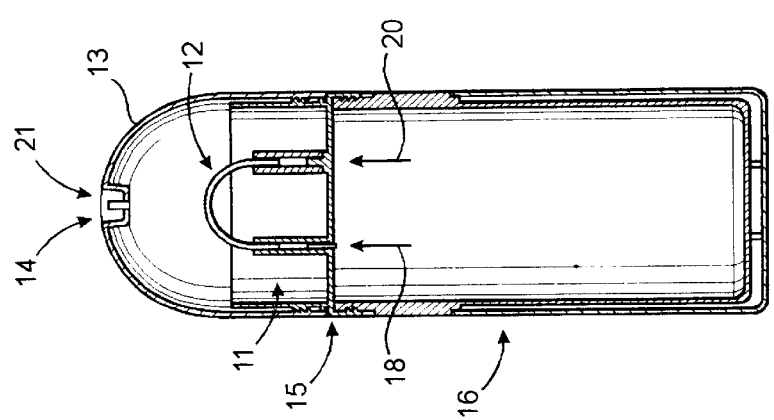

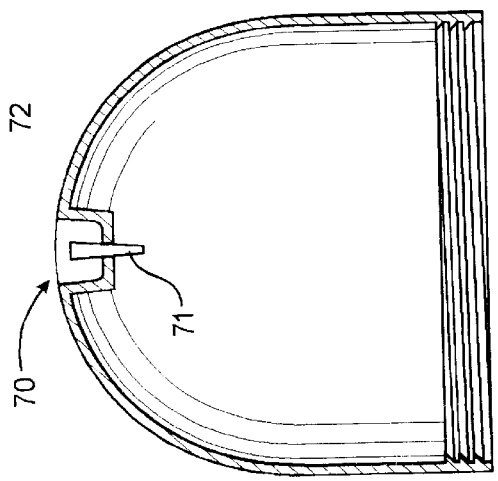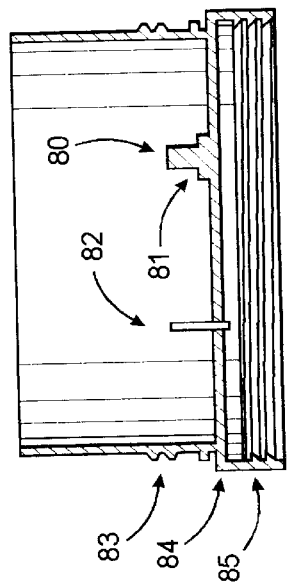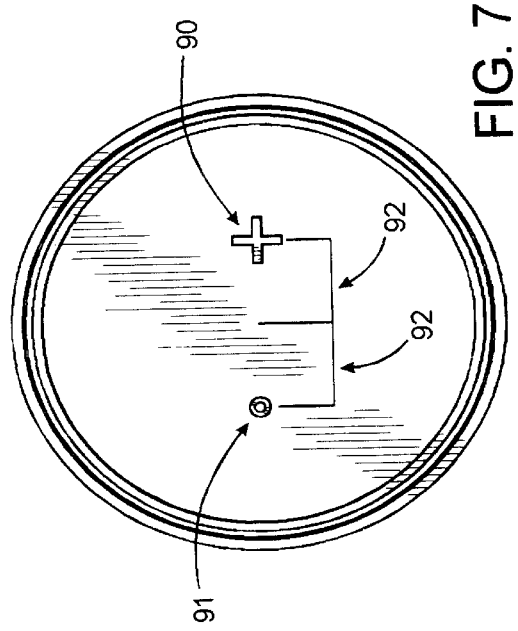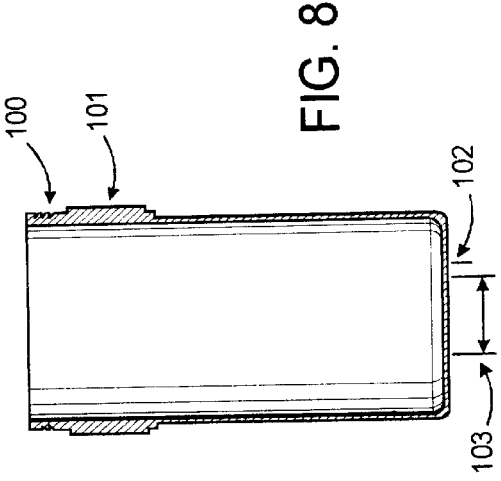

OXYGEN GENERATING DEVICE

BACKGROUND OF THE INVENTION

1. Field of the Invention

This invention relates generally to oxygen generation devices and more particularly to a chemical-generation, portable device usable by a patient or individual at home or in an emergency situation.

2. Description of the Prior Art

Oxygen generation devices are known in the art, however, they are either large, cumbersome, and difficult to use, necessitating that they be used in a medical office or hospital. Alternatively means of a size that can be used by a patient, such as high pressure oxygen cylinders are expensive, difficult to transport, and present an explosive or fire hazard.

SUMMARY OF THE INVENTION

The present invention is a oxygen generating device which comprises: a container having a mouth and a neck surrounding the mouth; a tank which has an annual flange for establishing a gas tight seal between the tank and the neck;

- a dome assembly which is engageable with the neck and extends upwardly to define a chamber above the neck (dome chamber); and
- means for permitting oxygen generated in the tank to flow into the dome chamber by bubbling through a liquid contained in the dome base;
- the dome base having an outlet connection through which oxygen can leave the tank and enter the dome and where at least part of the dome is transparent so as to render the inside thereof visible from the outside of the dome.

An object of the present invention is to provide a device usable by an individual or patient which generates a sufficient supply of oxygen for a wide range of applications. Another object of the present invention is to provide a chemical reaction oxygen generating device which may be refilled by the patient and is reusable or may be a one way, one time delivery system.

Other objects and advantages of the present invention will become apparent from the following description.

BRIEF DESCRIPTION OF THE DRAWINGS

FIG. 1 is a front elevation view in a cross-section of the inventive oxygen generation device.

FIG. 2 is a side elevation view of the generation device of FIG. 1.

FIG. 3 is a top plan view of the generation device of FIG. 1.

FIG. 4 is a perspective view of the oxygen generation device for the present invention.

FIG. 5 is a cross-sectional view of the dome portion of the generation device of FIG. 1.

FIG. 6 is a cross-sectional elevation of the dome base and the tank portion of the generation device of FIG. 1.

FIG. 7 is a top-sectional view of the dome base of the generation device of FIG. 1.

FIG. 8 is a cross-sectional side view of the tank portion of the generation device of FIG. 1.

FIG. 9 is a frontal cross-section view of the tank sleeve of the device of FIG. 1.

DETAILED DESCRIPTION OF THE EMBODIMENTS

Referring to FIG. 1, reference number 18 depicts an oxygen generating device which has an upper portion, dome assembly 13, and a lower portion, tank assembly 23, wherein tank assembly 23 comprises a cylinder having a neck 15, to which the dome assembly, dome, and dome base 13 is attachable.

Number 14 is the edge of the nipple fitting 21 located at the top of dome assembly 13. The nipple fitting advantageously is a recessed assembly. Item 11 is the water level inside dome assembly 13. Lower portion 23 contains a tank 17 where the reaction occurs to produce oxygen. In addition to the oxygen producing chemical(s), water is advantageously added to tank 17. Item 19 is the inlet for oxygen developed in tank 17. Oxygen is forced by pressure developed by its generation in tank 17 into inlet 19. Tubing 12 receives oxygen from tank 17 through fittings at inlet 19, and delivers oxygen through bubble fitting 20 into water present in the lower portion of dome assembly 13. Optionally a bubble restrictor plate can be fitted to the dome base to adjust or restrict the flow of oxygen or oxygen bubbles.

Item 16 indicates an insulating area, which may be a vacuum or advantageously may be a foam insulation layer between the receptacle and the receptacle sleeve. The oxygen generating reaction takes place inside the receptacle, with the sleeve forming an outside surrounding container for the receptacle.

Referring to FIG. 2, number 42 is a side view of tubing 12, number 43 refers to the intake valve and bubble fitting; and 44 is a fitting for the gasket at the intersection of dome assembly 13 and tank 17. Item 45 is a fitting for the gasket at the dome base, number 46 is a fitting for the tank sleeve for attachment to the tank, number 47 is the insulation area, which is advantageously filled with foam between the tank sleeve and the tank, and 40 is an optional means for keeping the tank from spinning in the tank sleeve.

Referring to FIG. 3, number 51 is the recessed area forming the outside of nipple 21 in the upper portion of dome assembly 13. Number 52 is the orifice of nipple 21, and number 50 is the edge of recessed area 51 which meets the surface of the dome at the outer edge of nipple 21.

Referring to FIG. 4, number 21 is the nipple at the top of dome assembly 13. Number 66 is the dome, number 62 is the dome base, number 63 is the top portion of the tank where it meets the dome assembly, 64 is the area where the tank meets the top of the tank sleeve, and 65 is the tank sleeve.

Referring to FIG. 5, number 70 is the edge of the recessed area in dome assembly 13 which forms nipple 21. Number 71 is the orifice on top of nipple 21 in the dome, and number 72 is the tube fitting for nipple 21.

Referring to FIG. 6, number 82 is the intake from the tank to dome assembly 13, number 83 represents the threads where the dome assembly attaches to the tank assembly, and number 84 is the shoulder which is set back to provide for a smooth contour and good fit so that the dome assembly overlaps the gasket to prevent it from being squeezed out. Number 85 represents the inside threads that connect to the tank assembly. Number 80 is the bubble valve assembly on the dome base and number 81 is a shoulder joint in the bubble valve assembly.

Referring to FIG. 7, number 90 is the bubble valve through which oxygen enters the water in the dome assembly, and number 91 is the intake orifice from the tank to the dome assembly. Advantageously 90 and 91 are equidistant from the center line of the dome, which distances are represented by 92 and 93.

Referring to FIG. 8, number 100 represents the threads in the gasket assembly inside of the tank assembly. Number 101 represents the area where the wall of the tank assembly is built up to accommodate the dome fitting over the edge of the gasket and allows for space between the tank sleeve and the tank in order to provide for the insulation area, and number 102 and 103 depict an optional fitting assembly on the base of the tank to prevent the tank sleeve from spinning in the tank.

Referring to FIG. 9, number 110 is the bottom rounded corner on the tank sleeve, number 111 is an optional fitting at the base of the tank sleeve which will prevent it from spinning in the tank, and number 112 is a fitting to facilitate the assembly process; i.e. to accomplish the tank holding itself in place while being moved through the manufacturing process.

Dome assembly 13 is advantageously manufactured from a clear or transparent material, preferably a polymer or plastic, and most preferably polycarbonate. Lower portion tank assembly 23 of the generating device advantageously may be made of opaque, clear or transparent material, preferably a polymer or plastic, and most preferably polypropylene.

In use, water is poured into the dome assembly and then into the tank to a point just below its intersection point with the tank assembly. The water level in the dome assembly is indicated by reference numeral 15. In addition, substance(s) which will react to produce oxygen are poured into tank 17. Advantageously such substances in powder or granule form. Dome assembly 13 is then screwed into tank assembly 23 and tightened, forming a gas tight seal.

Gaseous oxygen increases the pressure in tank 17 when generated by reaction of the substance(s) in tank 17 and is thereby forced upwardly through inlet 19, through tube 12, through fitting 20 and into the water in the dome base. The water that is in the dome base will humidify the oxygen before the oxygen exits dome 13 through nipple 21.

Dome 13 advantageously of a transparent material, therefore the production of oxygen and resultant bubbling will be visible from the outside of the dome. This will be evidence to the user that the device is working properly. Tank assembly 23 may be of an opaque material or transparent material. The arrangement of inlet 19, tube 12, outlet 20 and the diameter of dome 13, which advantageously approaches or is equal to the diameter of receptacle 17, prevents water or the oxygen producing chemicals from finding their way into nipple 21.

In addition, the present inventive device will generate oxygen at a sufficiently high pressure so that it can also be used with a nebulizer. In a nebulizer oxygen under pressure is passed through a liquid medication into a duct provided with a mouthpiece at one end. The present device allows a patient to breath through the mouthpiece and inhale the nebulizer medication. In the use of a conventional nebulizer, a pump is required where the nebulizing gas is air or, alternatively, a high pressure oxygen cylinder where the gas is oxygen. A high pressure oxygen cylinder is an expensive item of equipment, is difficult to transport, and presents an explosive or fire hazard. Such a cylinder cannot in most circumstances conveniently be kept by a patient at home or transported in remote areas. The oxygen generating device of the present invention can, however, in an inexpensive and effective manner, provide oxygen at a sufficiently high pressure to be used with a nebulizer. It is of light weight construction and can conveniently be kept by a patient at home, transported in remote areas and in emergency situations where there is no electricity available, which is not possibe with prior art devices.

What is claimed is:

1. An oxygen generating device comprising:
   a dome;
   a base attachable to the dome forming a dome assembly, having a volume for containing the reaction of an oxygen gas producing source and which partitions the oxygen gas producing source from the inside of the dome assembly;
   a tank assembly attachable to the dome assembly for containing the oxygen gas producing source;
   an inlet between said base and said dome whereby oxygen formed by the oxygen gas producing source in the tank assembly passes from said base into said dome;
   humidifying means for delivering oxygen from said inlet into water to humidify the oxygen within the dome, wherein said humidifying means is a tube formed in a U-shape connecting the inlet to a bubble fitting submerged in water in the dome; said bubble fitting comprising an outlet for the oxygen gas delivered from the inlet to bubble through the water into the dome; and,
   an outlet in said dome for delivering oxygen out of the dome.

2. The oxygen generating device according to claim 1, wherein said bubble fitting further comprises a cross-shaped outlet for delivering oxygen to bubble through the water.

3. An oxygen generating device comprising:
   a cylindrical tank assembly, said assembly having a mouth, a threaded neck surrounding the mouth, and a tank attachable thereto having an annular flange for establishing a gas tight seal between the tank and neck;
   said tank having sufficient volume to contain a chemical reaction therein which produces oxygen gas;
   a cylindrical tank sleeve into which the cylindrical tank fits so as to be surrounded by said sleeve;
   attachment means at the base of the sleeve for connecting the sleeve to the cylindrical tank;
   a dome;
   a base partitioning the cylindrical tank from the inside of the dome, said base having a threaded wall that screws into the dome, and said base attachable to the threaded neck of the cylindrical tank;
   a gasket between the dome and base;
   a gasket between the base and the cylindrical tank;
   an inlet in said base whereby oxygen gas from the tank passes through said base into said dome;
   a bubble fitting outlet for bubbling oxygen from the inlet through water in the humidifier dome;
   a tube formed in a U-shape connecting the inlet to the bubble fitting outlet; and
   a recessed nipple outlet in the top of the dome for delivering oxygen out of the dome.

4. The device according to claim 3, wherein said dome is transparent.

5. The device according to claim 3, wherein said attachment means at the base of the tank sleeve is a snap assembly.

6. The device according to claim 3, further comprising a space between the tank sleeve and tank.

7. The device of claim 6, wherein said space contains foam insulation.

8. A portable oxygen generator having an open top tank and a dome detachably mounted atop said open top tanks said dome having a bottom formed with an inlet, a tube mounted within said dome that extends upwardly from said inlet to a selected height above said bottom and then downwardly to a bubble fitting tube opening located adjacent said dome bottom, and wherein said dome has an outlet located above said selected height, whereby oxygen generated in the tank may be passed through a body of water with a surface level below the selected height in the dome to become humidified and out of the dome as a humidified stream of oxygen without water entering the tank.

* * * * *